(12) United States Patent
Budi

(10) Patent No.: US 12,115,170 B2
(45) Date of Patent: Oct. 15, 2024

(54) COMPOSITIONS AND METHODS OF CLOSTRIDIODIDES DIFFICILE TREATMENT, DECOLONIZATION, AND PREVENTION

(71) Applicant: Wisconsin Alumni Research Foundation, Madison, WI (US)

(72) Inventor: Noah Daniel Budi, Appleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/825,243

(22) Filed: May 26, 2022

(65) Prior Publication Data

US 2022/0378804 A1     Dec. 1, 2022

Related U.S. Application Data

(60) Provisional application No. 63/193,185, filed on May 26, 2021.

(51) Int. Cl.

| | | |
|---|---|---|
| *A61K 31/575* | (2006.01) | |
| *A61K 31/185* | (2006.01) | |
| *A61K 31/198* | (2006.01) | |
| *A61K 31/225* | (2006.01) | |
| *A61K 31/4164* | (2006.01) | |
| *A61K 31/444* | (2006.01) | |
| *A61K 31/65* | (2006.01) | |
| *A61K 31/7048* | (2006.01) | |
| *A61K 38/14* | (2006.01) | |
| *A61K 47/02* | (2006.01) | |
| *A61P 31/04* | (2006.01) | |

(52) U.S. Cl.
CPC .......... *A61K 31/575* (2013.01); *A61K 31/185* (2013.01); *A61K 31/198* (2013.01); *A61K 31/225* (2013.01); *A61K 31/4164* (2013.01); *A61K 31/444* (2013.01); *A61K 31/65* (2013.01); *A61K 31/7048* (2013.01); *A61K 38/14* (2013.01); *A61K 47/02* (2013.01); *A61P 31/04* (2018.01)

(58) Field of Classification Search
None
See application file for complete search history.

(56) References Cited

U.S. PATENT DOCUMENTS 10,550,437 B2   2/2020   Donskey et al.
2019/0046483 A1*  2/2019   James-Meyer ...... A61K 9/1271

FOREIGN PATENT DOCUMENTS

WO     WO-2020035720 A1 *  2/2020 ......... A61K 31/4164

OTHER PUBLICATIONS

Budi et al. "Omadacycline Compared to Vancomycin When Combined with Germinants To Disrupt the Life Cycle of Clostridioides difficile" Antimicrobial Agents and Chemotherapy 65:e01431-20. (Year: 2021).*
Kochan et al. "Intestinal calcium and bile salts facilitate germination of Clostridium difficile spores" PLoS Pathogens 13:e1006443. (Year: 2017).*
Budi et al. "Treatment issues in recurrent Clostridioides difficile infections and the possible role of germinants" FEMS Microbes 1:xtaa001. (Year: 2020).*
Begum, K. et al.; "In Vitro Activity of Amadacycline, a New Tetracycline Analog, and Comparators against Clostridioides difficile"; Antimicrobial Agents and Chemotherapy, vol. 64, Issue No. 8; 2020; 8 pages; DOI: https://doi.org/10.1128/AAC.00522-20.
Budi, N. et al.; "Omadacycline Compared to Vancomycin When Combined with Germinants To Disrupt the Life Cycle of Clostridioides difficile"; Antimicrobial Agents and Chemotherapy, vol. 65, Issue No. 5; 2021; 8 pages; DOI:https://doi.org/10.1128/AAC.01431-20.
Gallagher, J.; "Omodacycline: A Modernized Tetracycline"; Clinical Infectious Diseases, vol. 69, Issue Supplement 1; 2019; pp. S1-S5; DOI: https://doi.org/10.1093/cid/ciz394.
Singh, T. et al.; "Updates in Treatment of Recurrent Clostridium difficile Infection"; Journal of Clinical Medicine Research, vol. 11, Issue No. 7; 2019; pp. 465-471.

* cited by examiner

*Primary Examiner* — Sudhakar Katakam
*Assistant Examiner* — Zachary J Miknis
(74) *Attorney, Agent, or Firm* — Karen A. LeCuyer; De Witt LLP

(57) ABSTRACT

A germinant mixture includes a) a bile acid main germinant, b) an amino acid co-germinant, c) an edible spore solubilizing agent, and d) a divalent metal salt co-germinant. Also described is an oral pharmaceutical composition including the germinant mixture and a pharmaceutically acceptable excipient. A method of treating, decolonizing, and/or preventing *C. difficile* infection in the gastrointestinal tract of a patient in need thereof includes orally administering the germinant mixture or the oral pharmaceutical composition and an antibiotic that is active against *C. difficile* to the patient in need thereof.

20 Claims, 11 Drawing Sheets

COMPOSITIONS AND METHODS OF CLOSTRIDIODIDES DIFFICILE TREATMENT, DECOLONIZATION, AND PREVENTION

CROSS-REFERENCE TO RELATED APPLICATIONS

This application claims priority to U.S. Provisional Application 63/193,185 filed on May 26, 2021, which is incorporated herein by reference in its entirety.

FIELD OF THE DISCLOSURE

The present disclosure is related to germinant mixtures, pharmaceutical compositions and methods of treating, decolonizing, and/or preventing C. difficile infection in the gastrointestinal tract of a patient in need thereof.

BACKGROUND

Clostridioides difficile is the number one cause of hospital-acquired infections in the United States and one of the CDC's urgent-level pathogen threats. Hospital onset infections alone cost an estimated $1 billion in 2017, took 12,800 lives and caused 223,900 infections. The inflammation caused by pathogenic C. difficile results in diarrhea and pseudomembranous colitis. Approximately 25% of patients who undergo clinically successful treatment for this disease experience recurrent infection. After the first recurrence, the chance of a second recurrence increases to 45% and a third recurrence has a 65% chance or greater. Patients who do not experience a recurrence continue to asymptomatically shed spores 56% of the time, putting others at risk through environmental contamination. Current treatment options can eradicate the vegetative cell form of the bacteria, but do not impact the spore form, which is impervious to antibiotics and resists conventional environmental cleaning procedures. Antibiotics used in treating C. difficile infections (CDI) often do not eradicate the pathogen and can prevent regeneration of the microbiome, leaving patients vulnerable to recurrent CDI and future infections upon subsequent non-CDI-directed antibiotic therapy. Addressing the management of C. difficile spores in the gastrointestinal tract is important to make further progress in CDI treatment.

What is needed are novel treatments for C. difficile infections, particularly recurrent C. difficile infections.

BRIEF SUMMARY

In an aspect, a germinant mixture comprises a) a bile acid main germinant, b) an amino acid co-germinant, c) an edible spore solubilizing agent, and d) a divalent metal salt co-germinant.

In another aspect, an oral pharmaceutical composition comprises the germinant mixture and a pharmaceutically acceptable excipient.

In yet another aspect, a method of treating, decolonizing, and/or preventing C. difficile infection in the gastrointestinal tract of a patient in need thereof comprises orally administering the germinant mixture or the oral pharmaceutical composition and an antibiotic that is active against C. difficile to the patient in need thereof.

Figure 1:
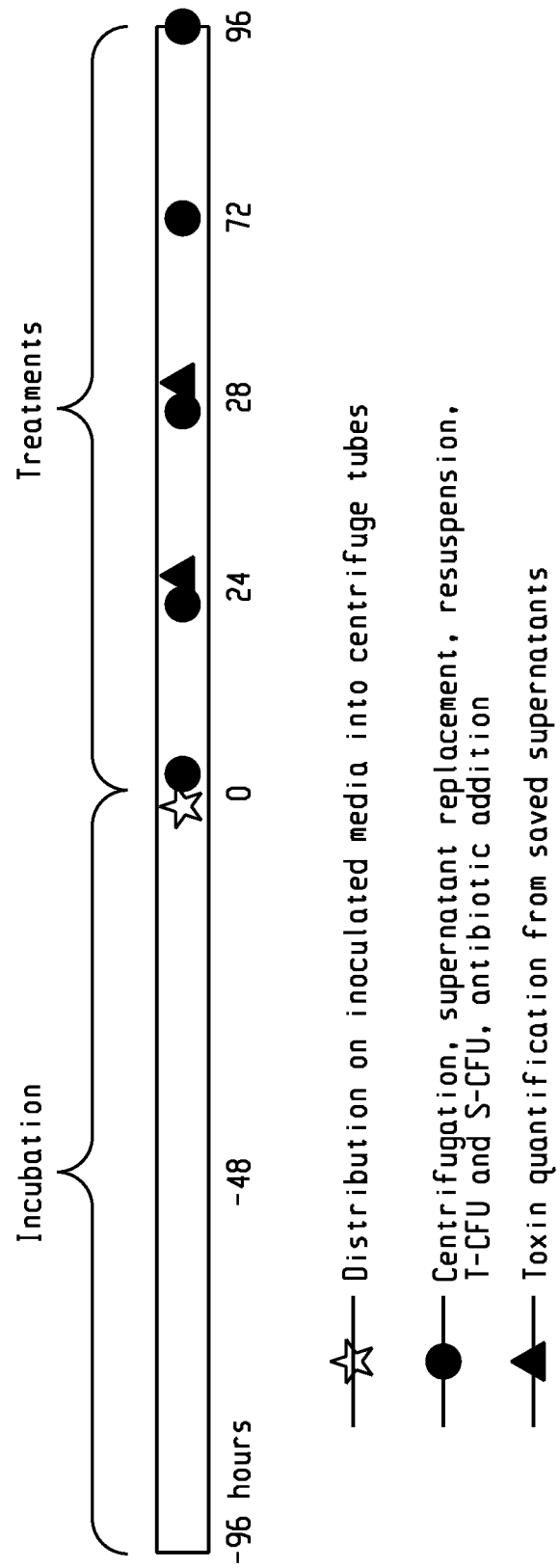
FIG. 1 is a schematic of incubation with C. difficile and treatments. Toxin quantification was done on all treatment samples for specified strains at 24 h and at 48 h for controls and if there was a change in (S-CFU).

The above-described and other features will be appreciated and understood by those skilled in the art from the following detailed description, drawings, and appended claims.

DETAILED DESCRIPTION

The treatment approach described herein to prevent recurrent CDI (rCDI) focuses on decolonizing patient gastrointestinal tracts of spores through oral administration of germinant mixtures. Germinants cause spores to turn into vegetative cells, which can be destroyed by antibiotic therapy. In addition to germinants, the mixture contains an edible spore solubilizing agent such as docusate, a common over the counter medication. The inventor discovered that docusate enhances germination while possessing antibiotic activity against *C. difficile*. This concept was tested in vitro and in a murine model, both showed decolonization. In the murine model, none of the mice given the germinant mixture experienced relapse, resulting in 100% survival, compared to 60% in those treated with a standard of care antibiotic, vancomycin, or omadacycline. All the mice experiencing CDI recurrence in the standard of care group, vancomycin, and omadacycline group died (40% mortality each).

In an aspect, it is expected that the treatment described herein will affect the gut microbiome to promote the growth of helpful bacteria in the gut. In a healthy host, the microbiome is able to prevent *C. difficile* spore germination and outgrowth of vegetative cells through resource competition and alteration of the bile acid profile. The microbiome's ability to prevent disease is called colonization resistance (CR). When CR is intact, ingestion of *C. difficile* spores does not result in mortality for mice. Without being held to theory, it is believed that docusate can inhibit *C. difficile* growth and help remove spores from the epithelial lining of the gastrointestinal tract without significantly affecting CR and thus function in CDI prevention.

In an aspect, a germinant mixture comprises a) a bile acid main germinant, b) an amino acid co-germinant, c) an edible spore solubilizing agent, and d) a divalent metal salt co-germinant.

The a) bile acid main germinant is the primary germinant signal and corresponds to a bile acid or salt thereof naturally found in human GI tracts. The bile acid main germinant turns spores to vegetative cells. Exemplary bile acid main germinants include taurocholate, glycocholate, a salt thereof, or a combination thereof. A specific bile acid main germinant is sodium taurocholate.

The b) amino acid co-germinant is expected to enhance the germination efficacy of the primary germinant and help induce natural bile acid production. The co-germinant may also boost the ability of the microbiome to fight infection. Exemplary amino acid co-germinants include taurine, glycine, or a combination thereof.

The c) edible spore solubilizing agent helps solubilize spores to detach them from the epithelium and mucus layer for easier excretion, prime spore germination, and may help remove toxins. Toxin B, the most dangerous toxin, is large and hydrophobic. In an aspect, the edible spore solubilizing agent comprises docusate, sucrose monolaurate, polysorbates, lecithin, or a combination thereof. Docusate, for example, is an edible soap typically used as a stool softener for opioid induce constipation. Docusate has antibiotic properties and increases germination rates. In an aspect, the docusate is sodium docusate or calcium docusate.

The d) divalent metal salt co-germinant increases the efficiency of the bile acid main germinant. Exemplary divalent metal salt co-germinants include a calcium salt such as calcium carbonate, calcium gluconate, calcium chloride, or calcium citrate. Calcium carbonate, for example, is advantageous as higher pH increases germination rates. In the mice, calcium gluconate was used as calcium carbonate is insoluble.

In an aspect, the germinant mixture comprises 1 to 5 grams, specifically 1.5 to 4 grams, more specifically 2 to 3 grams of component a); 1 to 6 grams, specifically 2 to 5 grams, more specifically 2.5 to 4 grams of component b); 200 to 600 milligrams, specifically 300 to 560 milligrams, more specifically 400-560 milligrams of component c); and 1 to 8 grams, specifically 2 to 5 grams, more specifically 3 to 4 grams of component d.

Exemplary ratios include 1 a: 1.5 b: 0.25 c: 1.5 d to 1 a: 1.2 b: 0.25 c: 2 d.

In an aspect, the germinant mixture comprises a) taurocholate, glycocholate, a salt thereof, or a combination thereof; b) taurine, glycine, or a combination thereof; c) docusate, sucrose monolaurate, polysorbates, lecithin, or a combination thereof; and d) a calcium salt. Exemplary calcium salts include calcium carbonate, calcium gluconate, calcium chloride, and calcium citrate.

In a specific aspect, a germinant mixture comprises a) sodium taurocholate, b) taurine, c) sodium docusate, and d) calcium carbonate.

In another aspect, a germinant mixture comprises a) sodium taurochlorate, b) taurine, c) calcium docusate, and d) calcium gluconate.

In an aspect, the germinant mixture further comprises an antibiotic such as an antibiotic that is effective against *C. difficile*. Exemplary antibiotics include vancomycin, omadacycline, fidaxomicin, ridinilazole, and metronidazole.

Omadacycline, for example, is a semisynthetic aminomethylcycline antibacterial derived from the tetracycline class of antibiotics that is less affected by the resistance mechanisms encountered for older tetracyclines. Omadacycline has been shown to be effective against vegetative *C. difficile*.

In an aspect, an oral pharmaceutical composition comprises the germinant mixture described herein and a pharmaceutically acceptable excipient. As used herein "pharmaceutically acceptable excipients" are well known to those skilled in the art and include diluents, preservatives, solubilizers, emulsifiers, and adjuvants.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

In an aspect, a method of treating, decolonizing, and/or preventing *C. difficile* infection in the gastrointestinal tract of a patient in need thereof, comprising, orally administering the germinant mixture or the oral pharmaceutical composition described herein and an antibiotic that is active against *C. difficile* to the patient in need thereof. Exemplary antibiotics are described above.

As used herein treating means administering, such as orally administering.

As used herein, decolonizing means reducing or depleting the *C. difficile* burden in the intestines.

As used herein, preventing means stopping *C. difficile* and/or *C. difficile* spores from colonizing the intestines of a patient.

In an aspect, the germinant mixture or oral pharmaceutical composition are administered one to two times daily after a symptom of *C. difficile* infection in the patient subsides.

In specific aspects, the germinant mixture or oral pharmaceutical composition are administered one to two times daily after *C. difficile* symptoms subside, for three to five days, followed one to two days of antibiotic only. In another aspect, antibiotics alone are administered prior to, and after, e.g. one, two, or three days, after administration of the germinant mixture or oral pharmaceutical composition.

In an aspect, the subject is suffering from recurrent *C. difficile* infection, defined as a relapse of CDI exhibiting symptoms within 2 to 8 weeks of successful treatment of the initial episode.

Exemplary symptoms of *C. difficile* infection include diarrhea, abdominal pain, fever, or a combination thereof.

In an aspect, the subject is suffering from recurrent CDI and the germinant mixture or oral pharmaceutical composition are administered one to two times daily after a symptom of CDI in the patient subsides. Typically, relapse CDI is caused by the same strain rather than a re-infection with a new strain. Risk factors for relapse CDI include advanced age, concomitant receipt of antacid medications, long hospital stays, and antibiotic use.

In an aspect, the patient is in a hospital or long-term care facility and the *C. difficile* infection follows administration of an antibiotic.

In another aspect, the patient has a positive stool sample test for *C. difficile*. Exemplary stool sample tests for *C. difficile* infection include polymerase chain reaction tests, a glutamate dehydrogenase (GDH) test, an enzyme immunoassay (HA) test, cell cytotoxicity assays, or a combination thereof.

The invention is further illustrated by the following non-limiting examples.

EXAMPLES

Materials and Methods

Bacterial strains and growth conditions: All growth media were reduced for a minimum of 24 h prior to use, and all manipulations took place within a type C vinyl anaerobic chamber (Coy Laboratory Products, Inc., Grass Lake, MI) using a gas mixture of 10% hydrogen and 10% carbon dioxide balanced with nitrogen. The chamber's hydrogen concentration was kept between 1 and 2%. *C. difficile* strains were plated onto *C. difficile* brucella agar (CDBA) from spore stocks and incubated for 24 h in the anaerobic chamber at 37° C. A single colony from each strain was used to inoculate 35 ml of brain heart infusion broth (BHI; Becton, Dickinson). *C. difficile* strains ATCC 1870 and ICCD 0715 were incubated in BHI for 48 to 96 h to achieve a spore concentration of about $1\times10^6$ spore CFU (S-CFU)/ml and about $1\times10^7$ total CFU (T-CFU)/ml, which captured both spore and vegetative cell growth. *C. difficile* VPI 10463 (ATCC 43255) and 630 (ATCC BAA-1382) were incubated for 96 h and conditioned anaerobically at 23° C. for 1.5 h on days two and three to achieve about $1\times10^5$ S-CFU/ml and about $1\times10^7$ T-CFU/ml. The temperature excursion for VPI 10463 and 630 was done to increase sporulation rates for a targeted starting concentration ($10^5$ to $10^6$ S-CFU/ml) and was not necessary for ATCC 1870 and ICCD 0715.

After incubation in 35 ml of BHI in a 50-ml centrifuge tube, or at time zero, 10 centrifuge tubes were filled with 1 ml of medium for duplicate treatments. T-CFU were determined daily for controls by dilution in pre-reduced $1\times$ phosphate-buffered saline (PBS) and plating on CDBA to ensure proper growth conditions. Total counts also were done for all treatment groups in ATCC 1870 to evaluate the continuous removal of vegetative cells with antibiotics. Dilutions for S-CFU were done daily for all treatments and controls in a 70:30 ethanol-$1\times$PBS mixture at a maximum ratio of 1:10 and allowed to settle for ≥15 min to remove vegetative cells before plating on CDBA. Dilutions plated on CDBA were anaerobically incubated for 24 h before enumerating T-CFU and S-CFU for ATCC 1870, VPI 10463, and 630. Counts were enumerated after 48 h for the clinical strain, ICCD 0715, which required increased incubation time to capture complete growth. VPI 10463 and 630 were evaluated because of their frequent use in animal models and for VPI's ability to produce large amounts of toxins. ATCC 1870 and ICCD 0715 represent R027 human epidemic strains. Baseline data about ATCC1870 indicated a high sporulation rate; only ribotype information was available for clinical isolate ICCD 0715.

To create the spore gavage on day 0, a spore stock containing VPI 10463 was plated onto *C. difficile brucella* agar (CDBA) and incubated anaerobically for 24 hours. A single colony was then suspended into 140 mL of brain heart infusion broth (BHI; Becton, Dickinson, Franklin Lakes, NJ USA). Incubation lasted 96 hours, being brought to 23° C. for one hour every 24 hours to induce sporulation. After incubation, 70 mL of inoculum was heat shocked at 60° C. for 20 minutes and the other 70 mL was pelleted and resuspended in a 70:30 ethanol-$1\times$PBS mixture for 15 minutes. Inocula were centrifuged, supernatants decanted, and all spore pellets were resuspended together in 28 mL of heat shocked supernatant. All centrifugations to pellet spores occurred at 3,000×g for ten minutes. This spore mixture was used to adjust $1\times$PBS to a concentration of $5\times10^5$ CFU/mL, which was aliquoted and frozen at −80° C. until use. Before each spore gavage, an aliquot of the mixture was diluted and plated onto CDBA to ensure no loss of spores occurred during storage.

Susceptibility testing: The minimum inhibitory concentration (MIC), defined as the lowest concentration of an antimicrobial that will inhibit the visible growth of a microorganism, was determined for all isolates. MICs to vancomycin and omadacycline were determined in triplicate by broth microdilution in reduced BHI containing 2-fold dilutions of antibiotics, similar to previous studies in the art. Microwell plates containing omadacycline and BHI were used on the same day as their creation, and all media were reduced for 24 h prior. Media used to inoculate plates were created by suspending 24-h colonies in BHI to a McFarland standard of 0.5, which was added to each well, sufficient to about $1\times10^6$ CFU/ml. A total volume of 200 ml was used, and plates were read after 24 h of incubation in the anaerobic hood. The lowest concentration without growth was determined to be the MIC. In accordance with CLSI recommendations, C. difficile ATCC 700057 was used as a control for each plate.

Time-kill curves: Time-kill curves follow the schematic shown in FIG. 1.

Experimental conditions included BHI alone (control), BHI with vancomycin or omadacycline (VAN and OMC), or BHI with germinants (BHIG) and antibiotics (VAN1G and OMC1G). BHIG consisted of sodium taurocholate 0.54% (Biosynth), glycine 0.23% (Fisher Scientific), calcium chloride dihydrate 0.0118% (Fisher Scientific), taurine 0.40% (RPI), and calcium docusate 0.01% (USP). BHIG medium was filter sterilized within the anaerobic chamber and frozen at $-20°$ C. Omadacycline at 25 mg/liter and vancomycin at 200 mg/liter were the antibiotic concentrations used in each treatment. These concentrations were chosen to reflect a midpoint between fecal concentrations reached during clinical dosing and our MIC values for C. difficile strain ATCC 700057. Fecal excretion of omadacycline is 81%, equating to approximately 430 mg/liter, and the MIC for ATCC 700057 was 0.125 mg/liter. Clinical dosing of oral vancomycin for CDI can achieve 2,000 mg/liter in the feces, while the MIC for 700057 was 2 mg/liter.

For each strain, starting T-CFU and S-CFU concentrations were similar between treatments. At time zero, baseline T-CFU and S-CFU samples were taken from the 35 ml of BHI that had been incubating for 48 to 96 h. One-milliliter samples from the 35 ml of incubated BHI then was distributed into 10 microcentrifuge tubes for duplicate treatments. The remaining inoculated medium from the 35-ml container was then discarded. Treatment samples were removed from the anaerobic chamber for centrifugation at 3,000×g for 10 min. After centrifugation, samples were returned to the anaerobic chamber and supernatant was removed and saved for toxin quantification. Centrifugation, supernatant removal, and resuspension were minimized to once daily, as spore washing increased our germination rates in pilot experiments and does not replicate in vivo conditions. Pellets were resuspended in fresh BHI or BHIG without antibiotics. Dilutions to capture T-CFU and S-CFU were taken after resuspension and before antibiotic addition. Centrifugation, supernatant removal, pellet resuspension in fresh BHI or BHIG, dilutions for T-CFU and S-CFU, and antibiotic addition were done sequentially every 24 h. This was done for 4 days unless S-CFU fell below the limit of detection ($1\times10^2$ CFU/ml) in any sample, at which the experiment was stopped, since no further germination would be detected. All samples were mixed via pipetting and vortexing for 15 s. Spore eradication was calculated as a percentage with the equation [(starting S-CFU−ending S-CFU)/starting S-CFU}λ100. Statistical significance for differences in germination between treatments was determined on log-transformed S-CFU concentrations at 96 h using analysis of variance and t tests.

Toxin quantification: To determine if germination increased toxin production during antibiotic treatment, C. difficile toxins were quantified in two strains from time-kill curve supernatants after 24 and 48 h of exposure (FIG. 1). C. difficile toxins A and B for strain 1870 and toxin B for ICCD 0715 and VPI 10463 were quantified separately by a C. difficile toxin A or B Quanti kit (tgcBiomics GmbH, Germany) using sandwich enzyme-linked immunoassay according to the manufacturer's instructions. ATCC 1870 and ICCD 0715 were chosen to represent human epidemic strains with increased sporulation, while VPI 10463 was chosen for its ability to produce large amounts of toxins. Toxin B production was concerning, as it is reported to be 100 to 1,000 more potent than toxin A ex vivo. All treatments were quantified at 24 h. Toxins were quantified at 48 h in controls and when germination was detected by a decrease in S-CFU/ml from time zero, because only vegetative cells can produce toxins. Combination toxin was not quantified, but the presence or absence of combination toxin genes cdtA and cdtB was confirmed with PCR, as shown in Table 1. Results were summarized by treatment groups using means and standard deviations. The equality of variances was tested using Bartlett's test. Linear regression was used to evaluate statistical differences between VAN and other treatment groups at the 24-h time point. All P values of #0.05 were considered statistically significant. STATA SE version 16 was used to analyze data.

Spore washing and germination: A single 24-h colony of each strain from CDBA was used to inoculate 35 ml of BHI and incubated anaerobically for 96 h at 37° C. Inoculated medium was then exposed to BHIG (without docusate) or BHI after four separate treatments: vegetative cell presence, heat shock, water washing, and docusate exposure. The first treatment, vegetative cell presence, was done anaerobically. After incubation, 35-ml cultures were split into four centrifuge tubes, 1 ml each, pelleted, and resuspended in reduced BHIG or BHI and incubated at 37° C. for 1 h before dilution in 70:30 ethanol-1×PBS mixture for S-CFU and 1×PBS for T-CFU. Dilutions for T-CFU were done to ensure vegetative cell presence. The next treatments, heat shock, water washing, and docusate exposure, all started with 5 ml of the 35-ml culture and were done aerobically except for the final step of plating for S-CFU. The 5-ml aliquots for these three treatments were all heat shocked at 60° C. for 20 min to destroy vegetative cells. The samples used for testing heat shock and germination were then aliquoted into four centrifuge tubes, resuspended in BHIG or BHI, incubated for 1 h, resuspended in 1×PBS, and heat shocked again before S-CFU enumeration. After heat shocking the water washing treatments, 5-ml samples were resuspended in sterilized water four times before being aliquoted into four centrifuge tubes. Samples were then resuspended in BHIG or BHI, incubated for 1 h, and resuspended in 70:30 ethanol-1×PBS mixture for plating in the anaerobic chamber. For docusate exposure alone, after heat shock, the 5-ml samples were resuspended in 0.5 mg docusate/ml water and allowed to sit at room temperature for 1 h. Docusate exposed samples were then aliquoted into four centrifuge tubes, resuspended in BHIG or BHI, incubated for 1 h, resuspended in 1×PBS, and heat shocked before S-CFU enumeration. All treatments were done in duplicate. Percent germination was determined by comparing samples exposed to BHIG versus BHI with the following equation: [(BHI S-CFU−BHIG S-CFU)/BHI S-CFU}λ100.

Animals: All experiments were approved by the University of Wisconsin Madison's Institutional Animal Care and Use Committee. Male C57BL/6 mice aged 5-8 weeks were purchased from Jackson Laboratory (Bar Harbor, ME USA) and housed in groups of five or three with sterile bedding and water. Mice were fed irradiated Teklad Global 16% protein rodent diets, catalog number 2916, throughout the experiment.

CDI Murine Models: This study evaluated antibiotics and germinants plus antibiotics in CDI models as previously described and detailed in FIG. 4. Both models began with antibiotics in drinking water (kanamycin 0.4 mg/ml, gentamicin 0.035 mg/mL, colistin 850 U/mL, metronidazole 0.215 mg/mL, and vancomycin 0.045 mg/mL) from day −6 to day −3, 72 hours total, and then switched to distilled water for the remainder of the experiment. Mice were given a weight based intraperitoneal (IP) clindamycin injection of 10 mg/kg on day −1 and 200 uL of the above spore mixture, totaling $1 \times 10^5$ spores, was administered via oral gavage on day 0.

In the severe model (FIG. 4A), mice were treated with omadacycline (OMC, n=10) or vancomycin (VAN, n=15) starting 30 hours post spore gavage and then once every 24 hours until day 5. Another group was given no CDI treatment as a positive control (infected untreated n=10). Lastly, a group was given antibiotic water and IP clindamycin, but no spore gavage or CDI treatment, as a negative control (uninfected untreated, n=5).

In the non-severe model (FIG. 4B), all CDI treatment groups were given omadacycline or vancomycin 6 hours after spore gavage on day 0. Half the mice were then treated with either once daily omadacycline or vancomycin until day 4 (OMC, n=13 and VAN, n=13). The other half received antibiotics with germinants (OMC+G, n=13 or VAN+G, n=13) once daily on days 1-3 followed by antibiotics only on day 4. This created four CDI treatment groups: OMC, VAN, OMC+G, and VAN+G. In addition, five infected untreated mice were used to ensure the same disease course as the severe model. No uninfected untreated mice were used in the non-severe model. Relapse was induced in the non-severe model by administering 10 mg/kg IP clindamycin on days 10, 11, and 12.

CDI Treatments: Mice in the VAN and VAN+G groups received VAN 1.5 mg while the OMC and OMC+G mice received OMC 0.25 mg daily during the CDI phase. The germinant groups also received 8 mg of sodium taurocholate, 10 mg of taurine, 0.2 mg of sodium docusate, and 1.72 mg of calcium gluconate given concomitantly with antibiotics on the specified days. All CDI treatments, antibiotics or antibiotics combined with germinants, were dissolved in 200 µL of sterile water and given via oral gavage.

Cage Changes: Complete cage changes, including water, food, and bedding, occurred in all groups of the severe model on day 3 and non-severe model on day 2 to remove as much environmental contamination as possible and prevent coprophagy of highly infectious stool. This allowed three antibiotic administrations in all CDI treatment groups and two antibiotic/germinant administrations in the VAN+G and OMC+G groups before cage changes. Therefore, any CDI relapses are likely attributed to an internal *C. difficile* and/or spore reservoir. Complete cage changes also occurred in the non-severe model on day 0, immediately after spore gavage.

Clinical Scoring, Weight Loss, and Survival: Clinical Scoring was comprised of six categories with higher scores corresponding to more severe disease as done previously with an added score of 4 for mice too sick to provide fecal samples. Mice with clinical scores of ≥14 were considered to have reached a humane clinical endpoint and were subsequently euthanized by $CO_2$ asphyxiation. Mice found dead by researchers were given a score of 20 on the day of mortality. Clinical scoring and weight loss were recorded throughout treatment.

Colon Histopathology: Three mice from OMC, VAN, OMC+G, and VAN+G in the non-severe model, and two uninfected untreated mice from the severe model were sacrificed on day 5 to obtain colons for histopathology. In addition, three mice in the infected untreated group that perished before day 5 were also harvested. The middle third of the colon was removed, flushed with 1×PBS, placed in coded tissue cassettes, and stored in formalin. Cassettes were submitted to a board-certified veterinary pathologist to assess edema, cellular infiltration, and epithelial damage, as done previously. The pathologist was blinded to all groups except the uninfected untreated and infected untreated groups. Scores ranged from 0-4 for all categories with higher scores representing more severe disease.

Bile Acid Quantification in the Non-Severe Model: Fecal bile acids were quantified by the University of Michigan Biomedical Research Core Facilities using negative liquid chromatography-electrospray ionization-triple quadrupole mass spectrometry. Two samples on day −6, before antibiotic water, and day 0, immediately before spore gavage, were evaluated. In addition, two samples from mice with median amounts of weight loss in OMC, VAN, OMC+G, and VAN+G on days 4 and 8 were evaluated.

Environmental Contamination and Day 15 Spore Shedding in the Non-Severe Model: On days 10 and 15 of the non-severe model, ethanol swabs were used to collect spores from each cage wall, water bottle, and middle of the food grate for each cage, totaling 12 swabs per treatment group. The length of each cage wall was wiped horizontally two inches above the floor. Individual fecal samples were also collected in the non-severe model on day 15. Ethanol swabs and fecal samples were placed in containers and put on dry ice until being transferred into a −80° C. freezer until use. For evaluation, swabs were allowed to dry aerobically for 24 hours before being placed in 4.5 mL of *C. difficile* brucella broth (CDBB) and incubated within the anaerobic hood. Fecal samples were washed twice in 1×PBS, resuspended in 1 mL 1×PBS, and half the resuspended fecal sample was added to 4.5 mL of CDBB. Swabs and fecal samples were incubated for one week, and those with color changes were streaked onto CDBA. Colonies with growth patterns and color changes characteristic of *C. difficile* were transferred to 1 mL containers of BHI, incubated for 24 hours, heat shocked at 95° C. for 10 minutes, and confirmed by PCR for toxin genes tcdA and tcdB. Mice that died prior to day 15, were too sick to provide samples, or had positive stool culture were considered positive for day 15 spore shedding.

DNA Extraction and Sequencing Analysis in the Non-Severe Model: Fecal pellets were used to extract DNA as described in the art. The V4 region of the 16S rRNA gene was amplified with PCR and sequenced on the Illumina MiSeq™ platform to generate 2×250 bp reads.

Paired-end demultiplexed sequences were checked for quality with FastQC and imported into QIIME 2 for initial processing following the moving pictures tutorial. Briefly, DADA2 was used to trim reads to 230 bp and create an ASV table. The Silva 138 classifier was used for taxonomic classification. Feature and taxonomy tables from QIIME2 were imported into R (version 4.0.5) and combined with the metadata with the Phyloseq package (version 1.34.0). The decontam package (version 1.10.0) was used to identify and remove contaminants based on prevalence. Phyloseq and microbiome (version 1.12.0) packages were used generate relative abundance plots.

Paired-end demultiplexed sequences were checked for quality with FastQC and imported into QIIME 2 for initial processing following the moving pictures tutorial. Briefly, DADA2 was used to trim reads to 230 bp and create an ASV table. The Silva 138 classifier was used for taxonomic classification. Feature and taxonomy tables from QIIME2 were imported into R (version 4.0.5) and combined with the metadata with the Phyloseq package (version 1.34.0). The decontam package (version 1.10.0) was used to identify and remove contaminants based on prevalence. Phyloseq and microbiome (version 1.12.0) packages were used generate relative abundance plots.

Example 1: Omadacycline Compared to Vancomycin when Combined with Germinants

Susceptibility testing: Table 1 describes strain-specific information and antibiotic susceptibility. *C. difficile* elicits disease upon the secretion of two toxins, TcdA and TcdB. Both VAN and OMC susceptibilities were within the quality control range for ATCC 700057 (VPI 11186). OMC MICs (0.031 to 0.125 mg/liter) were lower than VAN MICs (1 to 4 mg/liter) for the strains used in this study.

TABLE 1

DETAILS OF STRAINS

| Strain | Ribotype | Toxin genes | Vancomycin MIC (mg/liter) | Omadacycline MIC (mg/liter) |
|---|---|---|---|---|
| ATCC 700057 (VPI 11186) | R038 | None | 2 | 0.125 |
| 4118 (ATCC 1870) | R027 | tcdA, tcdB, cdtA, cdtB | 2 | 0.031 |
| ICCD 0715 (clinical strain) | R027 | tcdA, tcdB, cdtA, cdtB | 4 | 0.031 |
| VP1 10463 (ATCC 43255) | R087 | tcdA, tcdB | 1 | 0.063 |
| 630 (ATCC BAA-1382) | R012 | tcdA, tcdB | 4 | 0.125 |

*The presence or absence of combination toxin genes cdtA and cdtB was confirmed with PCR. For strains with an MIC range among the replicates, the highest concentration was reported.

Figure 2:
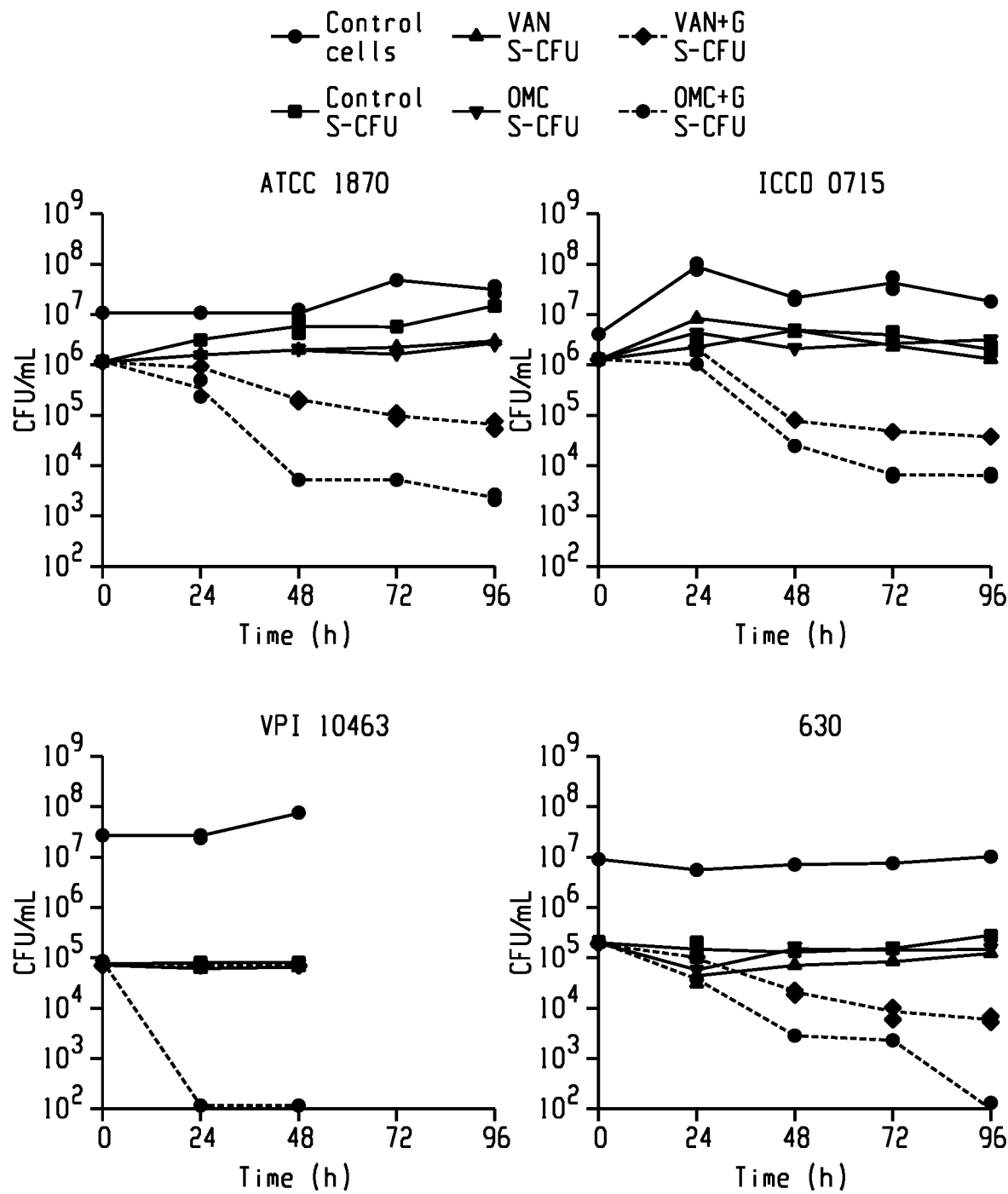
FIG. 2 shows time-kill curve results. (T-CFU) are only shown for controls. In VAN, OMC, VAN+G, and OMC+G samples, T-CFU equaled S-CFU from 24 to 96 h and are not shown for clarity. Control, BHI alone; VAN, vancomycin alone; OMC, omadacycline alone; VAN+G, vancomycin plus germinants; OMC+G, omadacycline plus germinants; TCFU, total vegetative cell and spore counts; S-CFU, total spore count.

Time-kill curves. Time-kill curves followed the schematic shown in FIG. 1. For BHI alone (growth controls), total numbers of CFU (T-CFU; vegetative and spore growth) and numbers of spore CFU (S-CFU) remained relatively constant during the 96-h treatment period in each strain (FIG. 2). This indicated vegetative cells had appropriate growth conditions for cell viability over the duration of the experiment. The only control with a notable change was the ATCC 1870 S-CFU/ml, increasing from $1.25 \times 10^6$ to $3.75 \times 10^7$ over 96 h. In ATCC 1870 antibiotic-treated samples, with or without germinants, T-CFU equaled S-CFU from 24 to 96 h, indicating both omadacycline and vancomycin were effective at killing vegetative cells, including those germinating from spores, throughout the experiment. Vegetative cell killing to below the limit of detection by omadacycline and vancomycin within a 24-h period is consistent with previously published time-kill curves. BHI conditions with VAN or OMC did not affect S-CFU throughout the treatment period in any of the four strains tested (FIG. 2).

Spore eradication in germinant-treated samples was most effective between 24 and 48 h in most strains, with only moderate further eradication noted from 48 to 96 h. Overall, the degree of spore eradication in germinant-treated samples varied by strain type and antibiotic. The R027 strains ATCC 1870 and ICCD 0715 had the lowest spore eradication in response to BHI with germinants (BHIG) at 96 h. Spore eradication in these R027 strains was 94.8 to 97.4% in VAN plus BHIG (VAN1G) and 99.4 to 99.8% in OMC plus BHIG (OMC+G). Higher levels of eradication were seen in 630, with 97.3% in VAN+G and 99.9% in OMC+G. All final OMC+G S-CFU in these strains were significantly lower than the VAN+G S-CFU (P, 0.005). Finally, VPI 10463 showed the highest level of spore eradication, reaching the limit of detection ($1 \times 10^2$ S-CFU/ml) at 24 h in both VAN+G and OMC+G.

Figure 3:
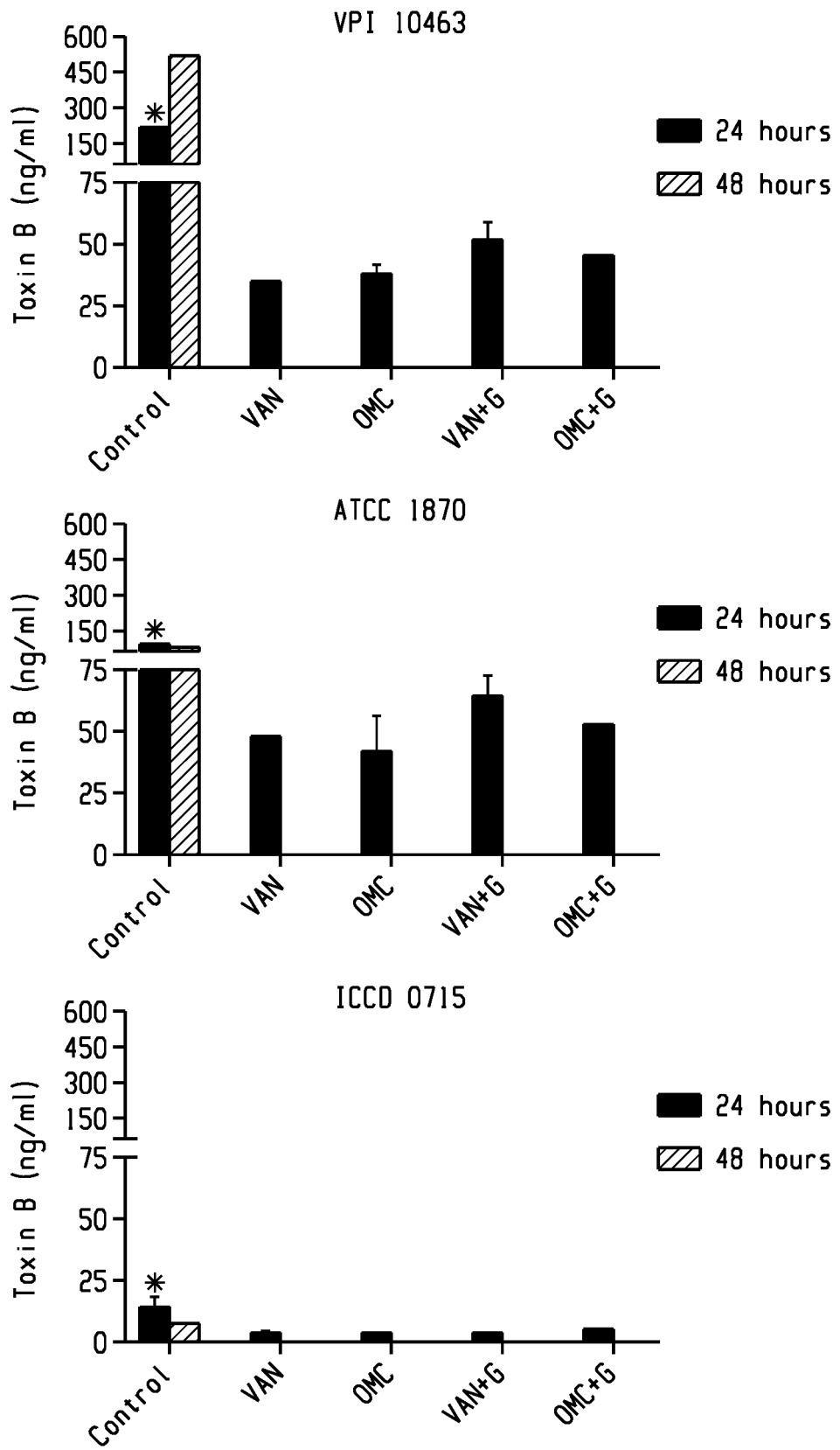
FIG. 3 shows toxin quantification at 24 h and 48 h of antibiotic treatment in the kill curve. VAN, vancomycin alone; OMC, omadacycline alone; VAN+G, vancomycin plus germinants; OMC1G, omadacycline plus germinants. An asterisk indicates a P value of 0.05 versus vancomycin treatment in 24-h samples.

Toxin production. ATCC 1870 and ICCD 0715 strains were chosen to represent human epidemic strains, while VPI 10463 was chosen for high toxin production. Toxin A and B production in ATCC 1870 and toxin B production in ICCD 0715 and VPI 10463 were quantified in all 24-h time-kill curve supernatants, while only control, VAN+G, and OMC+G were measured at 48 h, after the largest drop in S-CFU in ATCC 1870 and ICCD 0715 (Table 1). Control, VAN+G, and OMC+G levels were measured at 48 h because a reduction in S-CFU was noted, indicating that spores germinated into vegetative cells, which are capable of toxin production. The S-CFU reduction in BHIG samples between 24 and 48 h did not result in significant toxin B production, and most samples were below the limit of detection of 1.25 ng/ml (FIG. 3). Toxin A had similar results (data not shown).

Using VAN as the comparison group, only controls (BHI alone) had statistically significant increases in toxins at 24 h (P≤0.05). In addition, VAN was compared to VAN+G and OMC was compared to OMC+G at 24 h, and neither resulted in statistically significant differences in toxin production, indicating germination with these antibiotics did not increase toxin production.

Spore washing and germination. The time-kill experiments used a combination of vegetative cells and newly produced spores, more akin to the *C. difficile* growth cycle environment, while prior studies often purify spores before germination. Therefore, a spore-washing experiment was performed to investigate the influence of in vitro spore preparation and vegetative cell presence on germination rates. The results of vegetative cell presence, heat shocking, water washing, and docusate exposure on percent germination are summarized in Table 2. Vegetative cell presence prevented germination in all strains compared to the other treatments, with less than 10% germination for 630, ATCC 1870, and ICCD 0715. VPI 10463 spores had the highest germination (60%). This was similar to the results of the time-kill curves at 24 h, with VPI 10463 showing the highest germination rate in both experiments and negligible germination for the other strains. BHIG (without docusate) exposure did not change the T-CFU compared to that of BHI (data not shown). Heat shocking increased germination in all strains compared to vegetative cell presence. Four distilled water washes further increased germination, reaching above 90% in all strains. Lastly, 0.5 mg/ml docusate exposure achieved the highest percent germination compared to all other treatments. These results indicate that extrapolating germination rates from studies using purified spores to living systems may not be reflective of in vivo systems, where germination would be affected by vegetative cell presence and unconditioned spores.

TABLE 2

EFFECTS OF VEGETATIVE CELL PRESENCE, HEAT SHOCKING, WASHING AND DOCUSATE EXPOSURE ON PERCENT GERMINATION

| Condition | Germination (%) for: | | | |
|---|---|---|---|---|
| | 630 | VPI 10463 | ATCC 1970 | ICCD 0715 |
| Vegetative cell presence | 5.8 | 60.4 | −5.9 | −7.3 |
| Heat shock | 19.6 | >99 | 40.4 | 63.7 |
| Heat shock + 4 water washes | 91.7 | >99 | 95.7 | 97.0 |
| Heat shock + docusate (0.5 mg/ml) exposure | 92.8 | >99 | 98.2 | 98.6 |

Example 2: Experiments in a Murine Model

Figure 4:
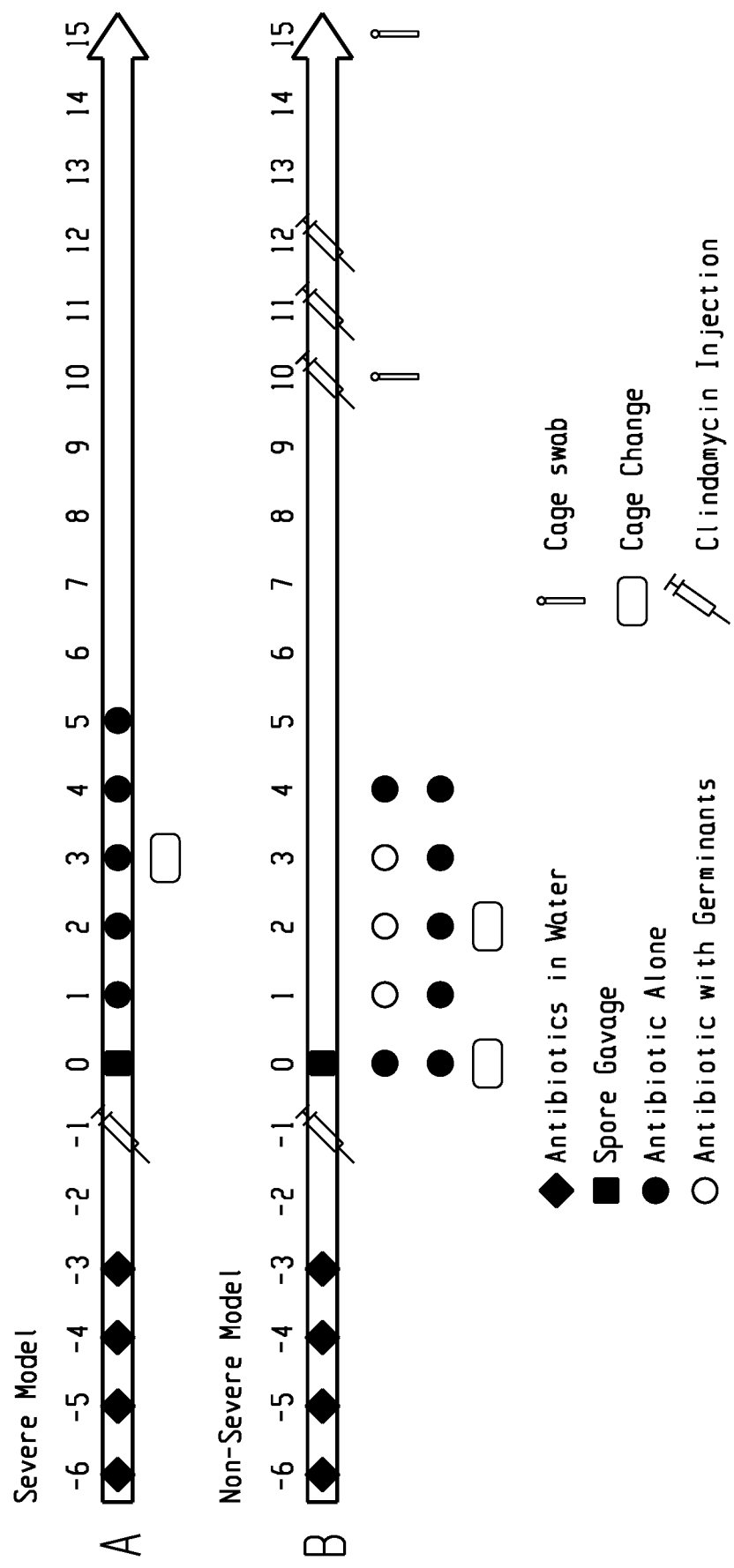
FIGS. 4A and B are model timelines: 4A. Severe model, treatments started 30 hours after spore gavage. Treatment groups included OMC (omadacycline), VAN (vancomycin), uninfected untreated, and infected untreated. 4B. Non-severe model, treatment started six hours after spore gavage. Treatment groups included OMC+G (omadacycline and germinants) VAN+G (vancomycin and germinants), OMC (omadacycline), VAN (vancomycin), and infected untreated. OMC+G and VAN+G both received antibiotics only on days 0 and 5 and concomitant germinants were given on days 1, 2, and 3.

The murine model is illustrated in FIG. 4. The murine model starts with antibiotics in drinking water for three days (noon on day −6 to noon on day −3). Regular water is given for the remainder of the model. No antibiotics are given on day −2. Clindamycin is given via an intraperitoneal (IP) injection on day −1. Administration of these antibiotics reduces the numbers of helpful bacteria in the GI tract, creating a niche for *C. difficile* to grow into.

Spores are given on day 0. In the model in which germinants are used, spores are given six hours before antibiotics to allow time for colonization. Six hours past the spore gavage on day 0, only antibiotics (omadacycline, OMC or vancomycin, VAN) are administered. Antibiotic treatment should be established before germinant (G)/antibiotic combinations (OMC+G and VAN+G) are given. The germinant treatment consisted of 8 mg taurocholate, 10 mg taurine, 0.2 mg sodium docusate, and 17.2 microliters of 10% calcium gluconate given to mice via oral gavage with either 0.25 mg omadacycline or 1.5 mg vancomycin dissolved in water. The total volume of each individual oral gavage, for all treatment groups, was 200 microliters. On day 2, half the mice continued with antibiotic only treatment and half were treated with OMC+G or VAN+G. Antibiotic and germinant treatments were given on days 1, 2, and 3 for the germinant groups followed by antibiotics alone on day 4. This is a total of 5 days. The antibiotic only groups were treated from day 0 to day 4.

The reason for sandwiching germinant/antibiotic treatment is to have antibiotic presence before germinants arrive to prevent outgrowth of vegetative cells that could lead to clinical deterioration. Likewise, antibiotic only treatments are done last (day 4) in all groups to kill vegetative cells that may have resulted from the previous days' germinants.

Figure 5:
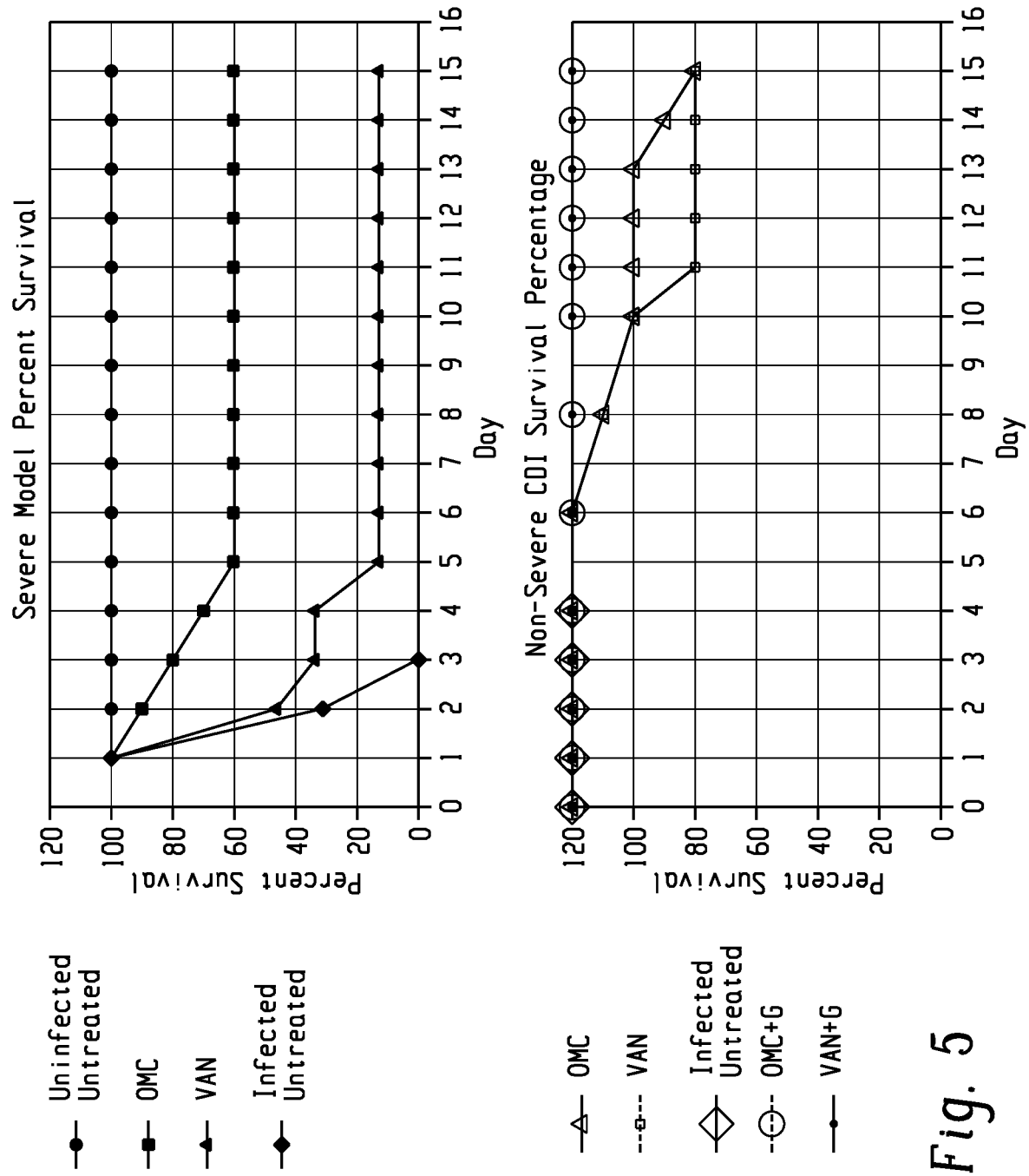
FIG. 5 shows survival percentage. OMC=omadacycline group, VAN=vancomycin group, OMC+G=omadacycline and germinant group, VAN+G=vancomycin and germinant group, uninfected untreated, infected untreated.

Survival, Clinical Scoring, and Weight Loss: Survival is displayed in FIG. 5 while clinical score and weight loss are presented in FIG. 6. In both models, all the infected untreated mice perished by day 3. The uninfected untreated mice, survived until the end of the experiment, showing no signs or symptoms of CDI. In the severe model, day 15 survival was significantly higher in OMC (60%), compared to VAN, (13.3%) (P=0.028). Weight loss and clinical scoring were higher in VAN compared to OMC throughout the study, indicating more severe disease progression.

*C. difficile* is known for its ability to cause relapse. Relapse *C. difficile* infections (rCDI) are caused by spores that remain in the GI tract or are taken up from the environment in mice that do not have healthy microbiomes. Relapse was seen in the antibiotic only groups starting around day 6, after much of the antibiotics were washed out of the GI tract. Relapse was not observed in the germinant treated groups. By day 10, 20% of the OMC and VAN groups had succumb to rCDI.

Figure 6A:
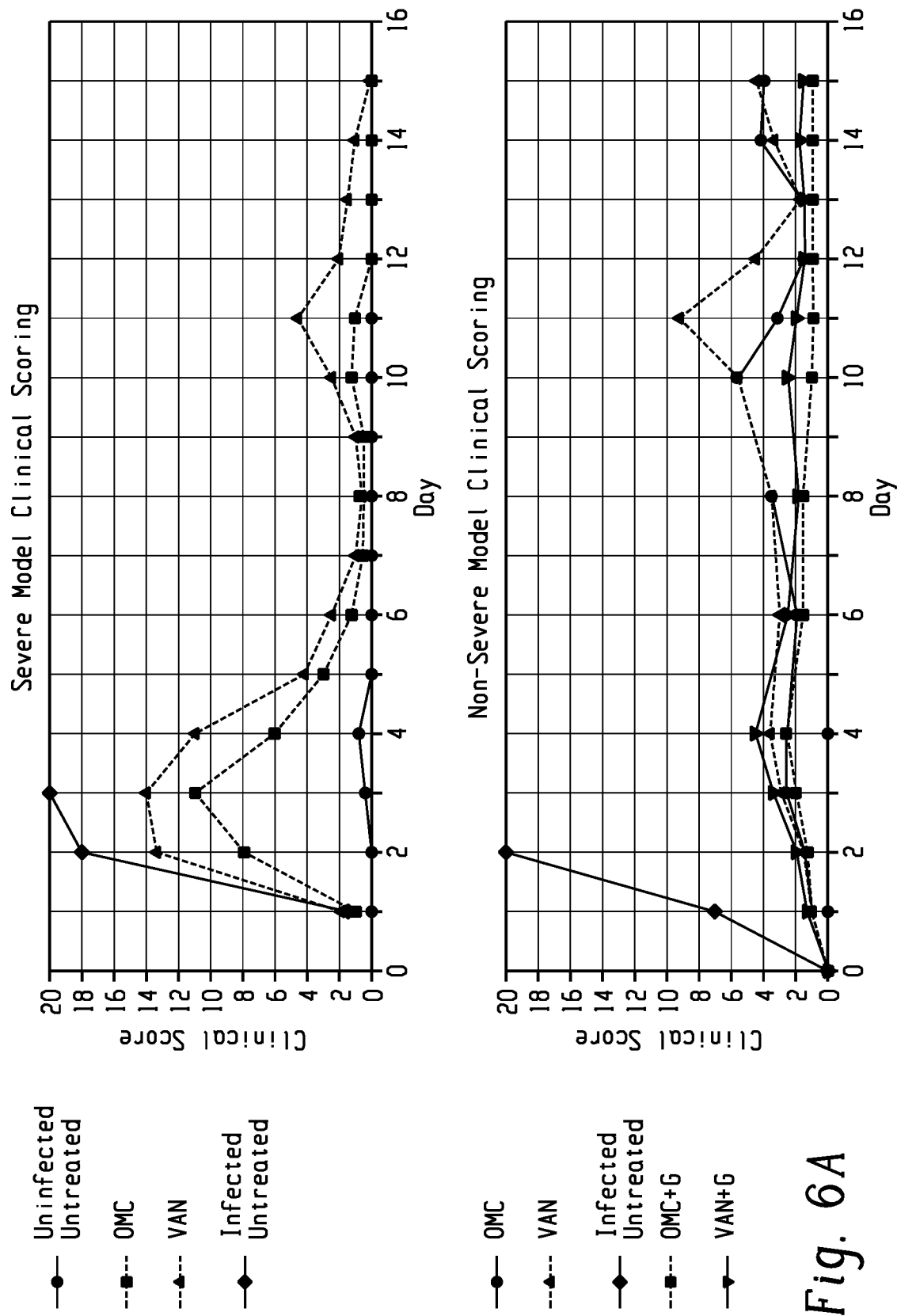
FIGS. 6A and B show results of clinical scoring and weight Loss. OMC=omadacycline group, VAN=vancomycin group, OMC+G=omadacycline and germinant group, VAN+G=vancomycin and germinant group, uninfected untreated, infected untreated.
Figure 6B:
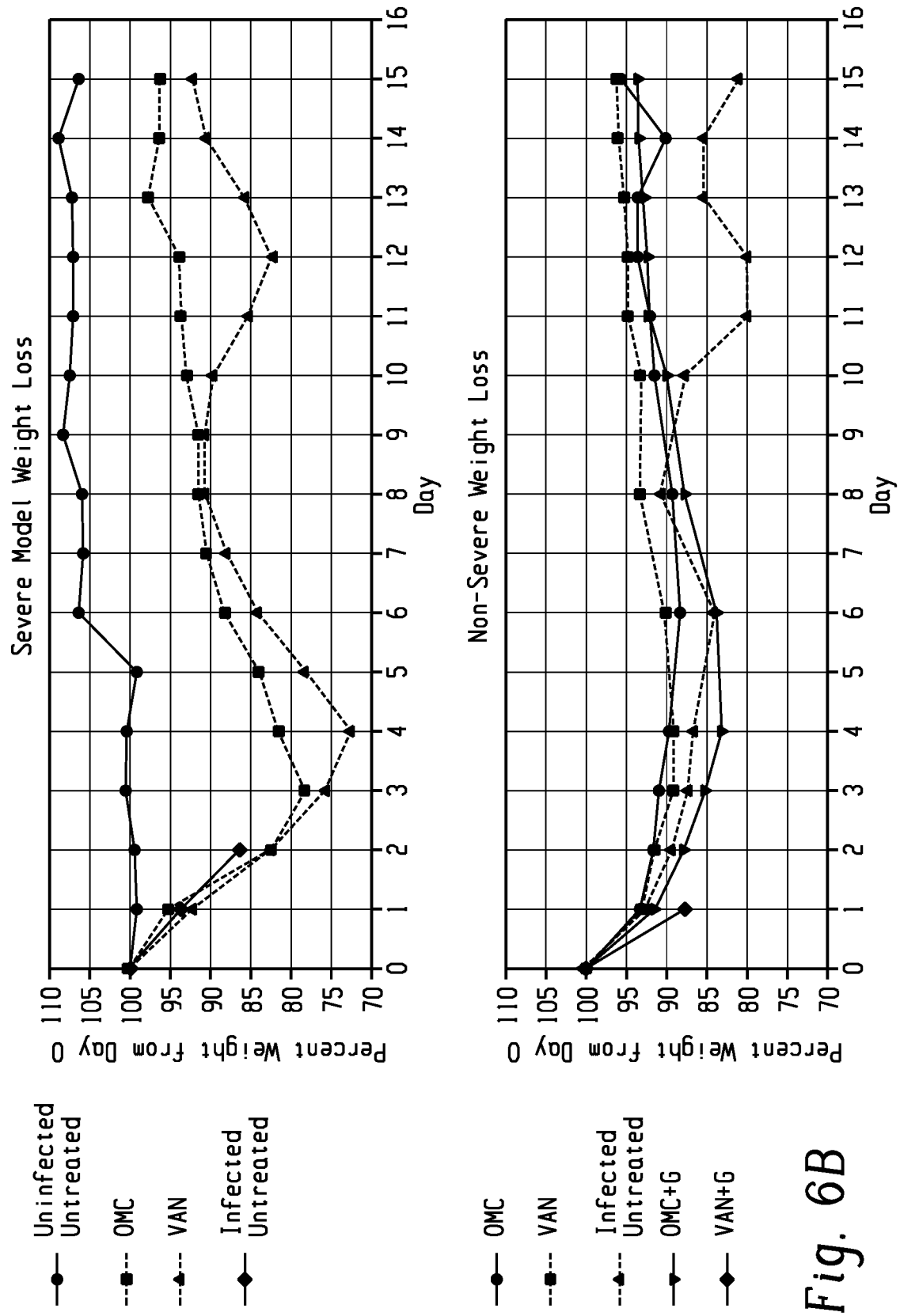

In the non-severe model, no deaths occurred during treatment. Post treatment survival was similar for VAN and OMC until day 11 when clindamycin-induced relapse (to induce rCDI, all groups were given clindamycin IP injections on days 10, 11, and 12) caused an immediate survival drop in VAN but not in OMC. Notably, none of the OMC+G or VAN+G mice died from, or showed signs of, rCDI. Final survival was 60% for antibiotic alone (OMC, 6/10, and VAN, 6/10) and 100% for antibiotic plus germinants (OMC+G, 9/9 and VAN+G, 8/8) (P<0.001). Clinical scoring and weight loss for germinant-antibiotic treated mice were similar to respective antibiotic alone groups until day 8, with VAN and VAN+G showing more disease than OMC and OMC+G (FIG. 6). Clindamycin-induced relapse only appeared to affect OMC and VAN, and not OMC+G or VAN+G, as noted by increased weight loss and clinical scoring in the non-germinant treated groups.

Figure 7:
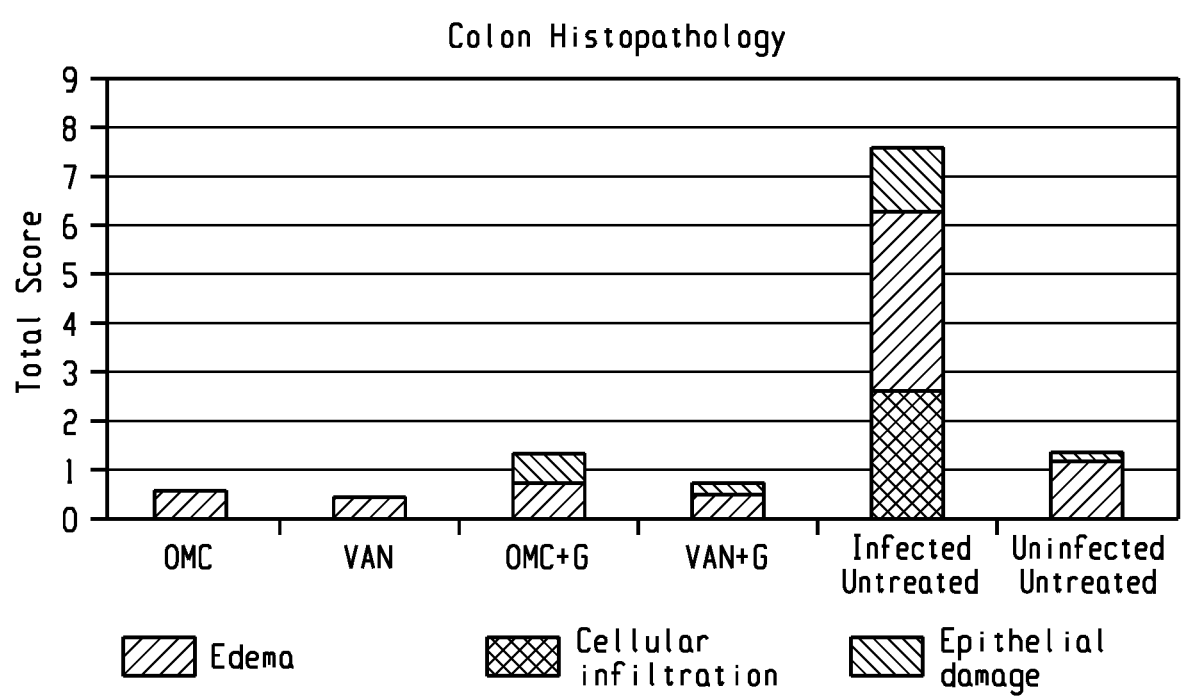
FIG. 7 shows day five colon histopathology. OMC=omadacycline group (n=3), VAN=vancomycin group (n=3), OMC+G=omadacycline and germinant group (n=3), VAN+G=vancomycin and germinant group (n=3), were taken from mice in the non-severe model. Uninfected untreated (n=2) were taken from the severe model and infected untreated (n=3) were taken at time of death before day 5.

Colon histopathology: Day 5 colon histopathology results are summarized in FIG. 7. No sizable difference in overall scores between uninfected untreated and the treatment groups occurred, suggesting that both antibiotics, if given early enough, were able to prevent damage from vegetative cells, and germinants did not cause excessive colonic deterioration. The infected untreated group displayed the most damage and was similar to previous studies in this mode.

Figure 8:
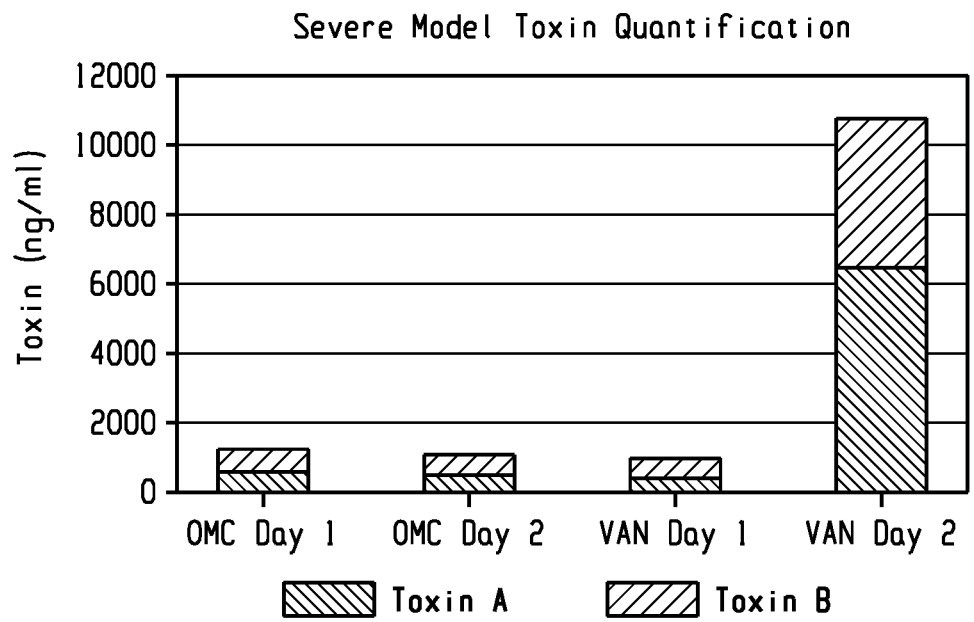
FIG. 8 shows toxin quantification of treatment groups. OMC=omadacycline group, VAN=vancomycin group, OMC+G=omadacycline and germinant group, VAN+G=vancomycin and germinant group.
Figure 8:
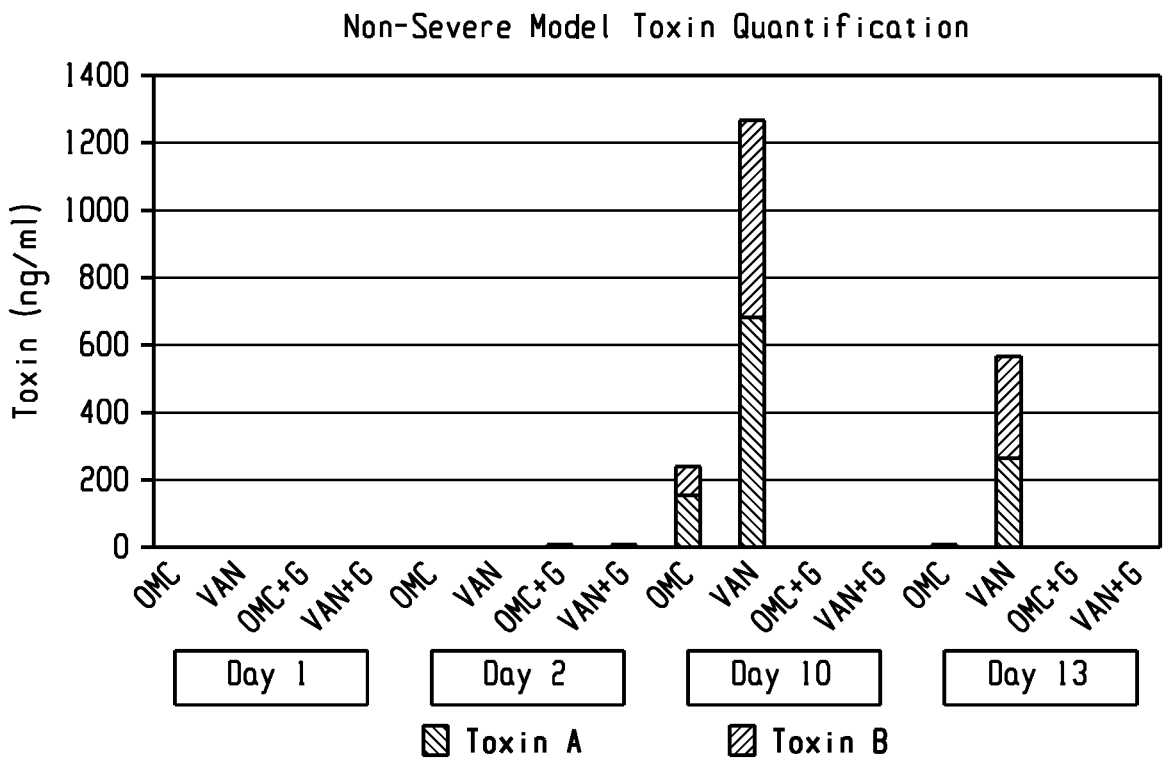

Toxin quantification: FIG. 8 shows a summary of toxin quantification for both models. In the severe model, the same three mice were used on day 1 and 2. Toxin amounts were similar between OMC and VAN on day 1. On day 2, median toxin A and B production was significantly higher with VAN versus OMC (P=0.004) and correlates with higher mortality in VAN at this time point. In the non-severe model, both antibiotics, given on day 0, prevented toxin production on day 1. The first administration of germinants and antibiotics in OMC+G and VAN+G, on day 1, did not result in notable toxin production on day 2. Day 10 and 13 toxin amounts were higher in VAN compared to OMC and absent from OMC+G and VAN+G. All samples in the severe model and non-severe model that were positive for toxin production were also positive for spore shedding (data below).

Environmental Contamination and Spore Shedding in the Non-Severe Model: Both OMC and VAN had 8.3% positive cage swab rates on day 10, compared to 0% in OMC+G or VAN+G. On day 13, 25% of cage swabs from VAN treated mice were positive. There were no positive swabs in OMC, OMC+G, or VAN+G on day 13.

For spore shedding at day 15 in the non-severe model, 100% of VAN-treated mice were positive for *C. difficile* spores versus 60% for OMC-treated mice (P=0.087). Notably, none of the OMC+G or VAN+G mice were positive for *C. difficile* spores versus 80% spore positivity with antibiotic alone (P<0.0001).

Figure 9:
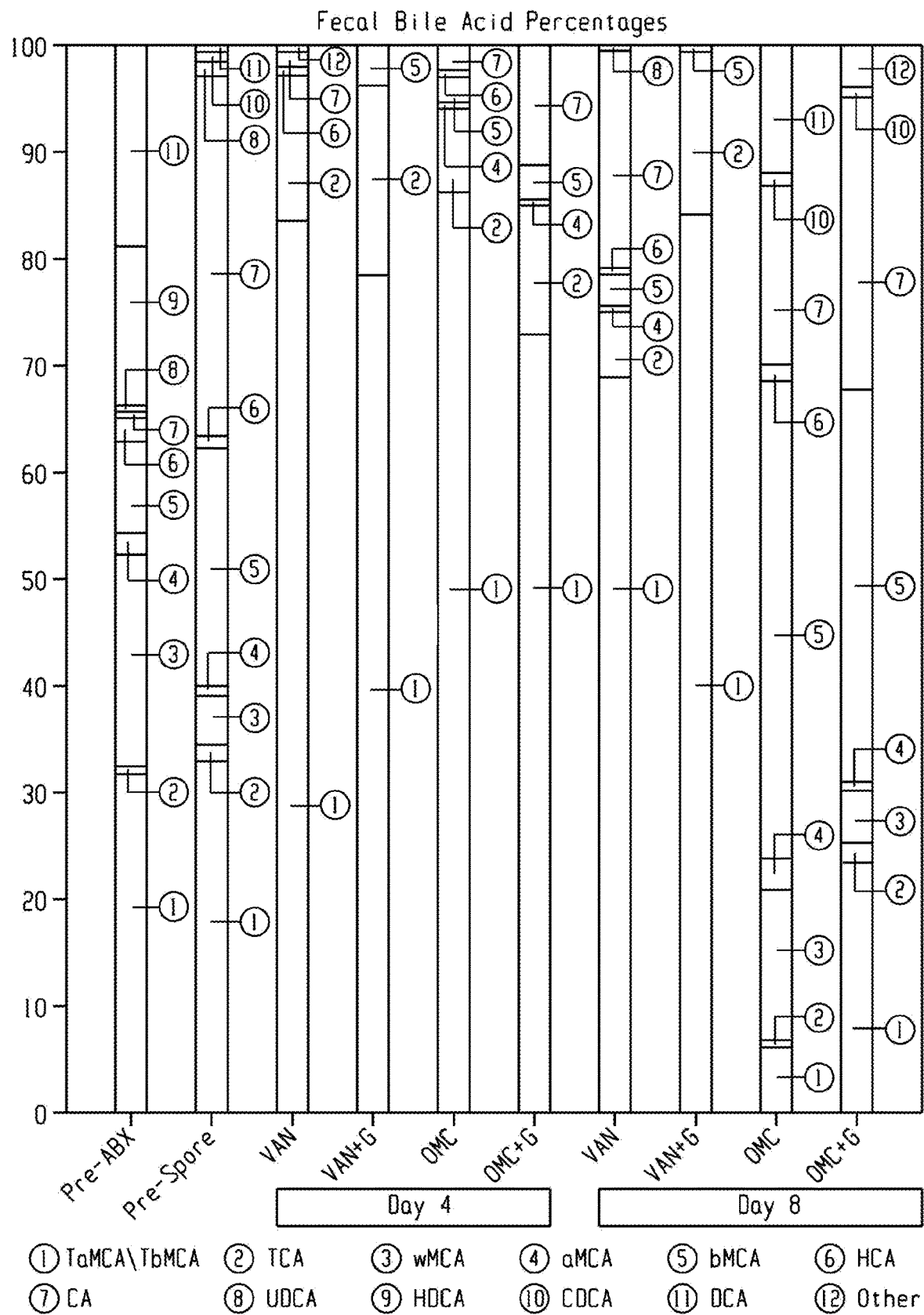
FIG. 9 shows fecal bile acid percentages for two mice in each group. Pre-ABX=fecal samples taken before antibiotic water, Pre-Spore=fecal samples taken directly before inoculation, OMC=omadacycline group, VAN=vancomycin group, OMC+G=omadacycline and germinant group, VAN+G=vancomycin and germinant group, TaMCA\TbMCA=tauro-alpha or beta-muricholate, TCA=taurocholate, wMCA=omega-muricholate, aMCA=alpha-muricholate, bMCA=beta-muricholate, HCA=hyocholic acid, CA=cholate, UDCA=ursodeoxycholate, CDCA=chenodeoxycholate, DCA=deoxycholate, Other=bile acids comprising of <1%.

Fecal Bile Acid Quantification in the Non-Severe Model: Percentages of bile acids are summarized in FIG. 9. Bile acids concentrations are highly regulated by the human body. About 95% of bile acids secreted into the GI tract are recycled. Bile acid diversity in the GI tract is largely controlled by the microbiome. Humans produce primary bile acids, such as cholate, which can be conjugated with amino acids, such as taurine, to create taurocholate. The microbiome can edit primary bile acids into secondary bile acids. Certain primary and secondary bile acids can prevent *C. difficile* germination and outgrowth. The levels of secondary, *C. difficile* inhibiting, bile acids are decreased in microbiomes that have been exposed to certain antibiotics while taurocholate, a bile acid that induces germination, is increased. Shifts in bile acid pool composition post antibiotic exposure often favor *C. difficile* growth, but do not allow for complete germination of spores. FIG. 9 shows that bile acid levels before any antibiotics (day −6) are more diverse compared to day 0 and contain more secondary and deconjugated bile acids. By day 4, much of the bile acid diversity is gone in all treatment groups with VAN and VAN+G showing less diversity than OMC or OMC+G. Over 95% of the bile acid pool in all groups on day 4 consists of primary bile acids, most of which are conjugated. By day 8, VAN and VAN+G still show limited diversity, mostly unchanged from day 4, while bile acid diversity with OMC and OMC+G was diverse, particularly the secondary deconjugated bile acid omega-muricholate. The germinant treatment did not appear to alter the bile acid pool compared to antibiotic only treatments. Vancomycin has been shown to induce bile acid changes that favor *C. difficile* growth through microbiome destruction. The similarities in bile acid profiles between VAN and VAN+G on day 8 suggests *C. difficile* should be able to grow in both treatment groups. The lack of *C. difficile* signs and symptoms in the VAN+G mice, compared to the high mortality in VAN, suggests the organism was not present in the VAN+G group and thus unable to cause rCDI. Omadacycline appears to facilitate the return of bile acid diversity, likely through microbiome regeneration. The lack of bile acid changes between germinant and antibiotic only groups suggests that the amount of taurocholate administered in germinant groups was not taken up in substantial amounts, and was excreted before fecal samples were taken the following day.

Figure 10:
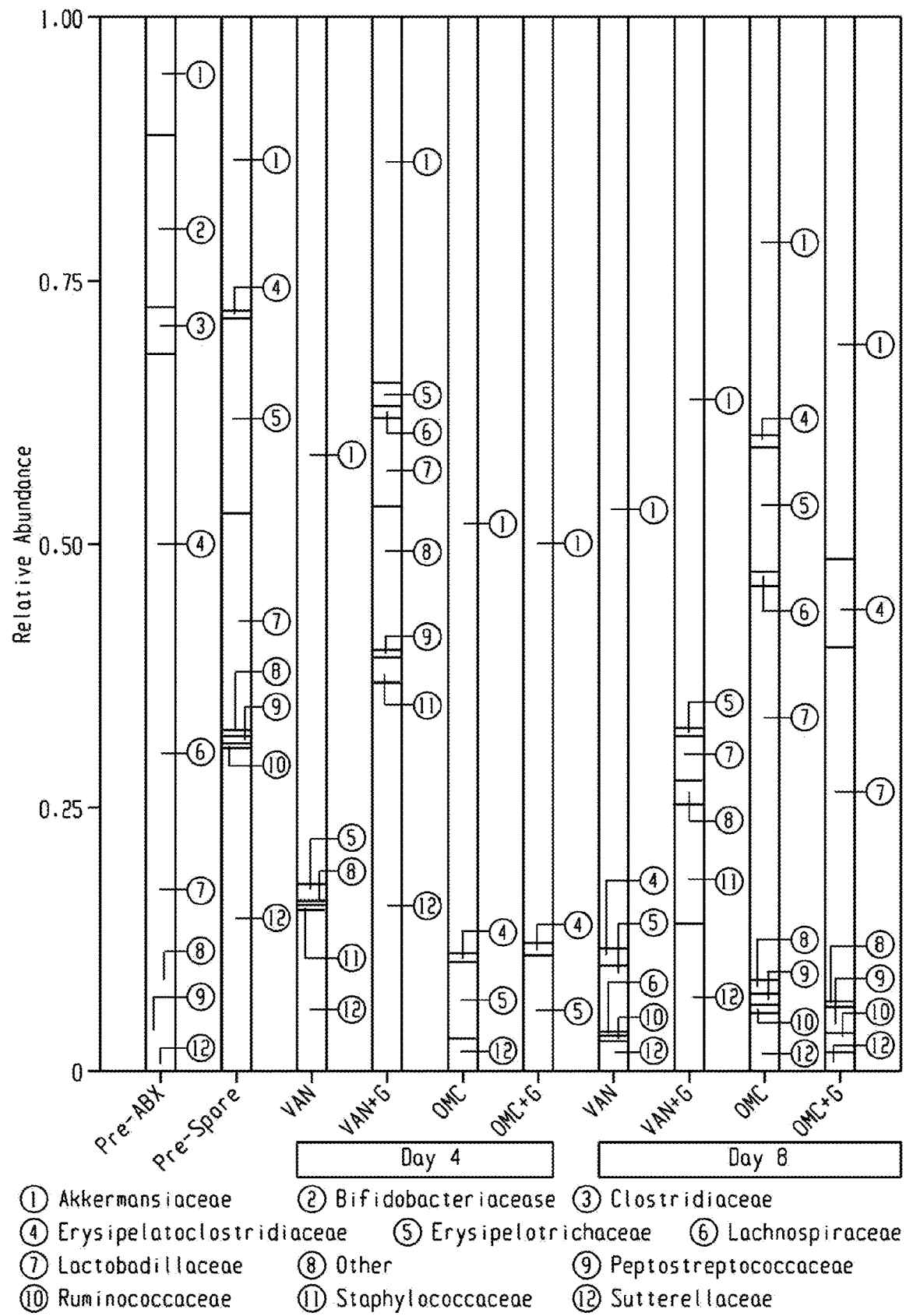
FIG. 10 shows fecal 16S Sequencing in the Non-Severe Model. Pre-ABX=fecal samples taken before antibiotic water (n=8), Pre-Spore=fecal samples taken directly before inoculation (n=52), VAN=vancomycin group (day 4 n=11, day 8 n=7), VAN+G=vancomycin and germinant group (day 4 n=8, day 8 n=6), OMC=omadacycline group (day 4 n=11, day 8 n=6), OMC+G=omadacycline and germinant group (day 4 n=9, day 8 n=7).

Fecal 16S Sequencing in the Non-Severe Model: Microbial diversity on day −6, pre-antibiotic water, was greater than that of day 0, pre-spore gavage, and day 0 was greater than day 4 (FIG. 10). On day 4, VAN+G displayed the most diversity. Vancomycin treatment groups appeared to prevent much of the microbial diversity from returning compared to omadacycline treatment groups on day 8, aligning with the fecal bile acid quantification data.

DISCUSSION

Recurrent *C. difficile* infections are devastating for patients and current antibiotic treatments are not effective at spore removal, a major contributor to rCDI. In lieu of colonization resistance, fecal transplants may be the most efficacious treatment but come with concerns of transmitting infectious organisms and has limited durability during subsequent antibiotic treatment. Another potential mechanism for treatment, besides fecal transplantation or antibiotics alone, is anti-germinant administration. Previous attempts have been unsuccessful likely due to use of anti-germinants that prevent spores from turning into toxin producing vegetative cells, but do not aid in their removal from the gastrointestinal tract, thereby preserving the spore reservoir until a time of non-adherence. Herein described is a novel method for vegetative cell and spore decolonization which produces a durable response without the need for continuing CDI-directed treatment even during subsequent recurrence.

Germinant-antibiotic combinations prevented rCDI associated mortality, toxin production, and spore shedding compared to antibiotics alone. This suggests mice were effectively decolonized at the end of treatment. Because environmental contamination was removed via cage changes, relapses were likely due to spores attached to animal fur or gastrointestinal surfaces. Considering the similarities in bile acid profiles and 16S results, germinant treated mice should have been equally susceptible to rCDI from externally attached spores, making an internal reservoir more likely.

In vitro data show that antibiotics alone do not alter spore concentrations, but germinant addition, particularly with omadacycline, was able to remove >99% of spore colony forming units in R027 strains without increased toxin production.

Antibiotic only treatments the day before and after germinants was to ensure the safety of the germinant co-administration regimen. This was designed to mitigate the risk of initial germination, without established antibiotic presence to kill vegetative cells, which may result in increased toxin production. Continuing antibiotics one day after germinant was to mitigate the concern for germination on the last treatment day, promoting vegetative cell presence as antibiotic concentrations dwindle. Buffering germinant/antibiotic administration on days 1, 2, and 3, with antibiotics alone on days 0 and 4, appeared to alleviate these concerns and would be translatable to clinical infection management.

Though either germinant antibiotic combination prevented rCDI, omadacycline appeared to be more efficacious in lessening disease severity. This was especially evident in the severe model, with lower mortality corresponding to decreased toxin production, clinical scoring, and weight loss. Similar results were found in the non-severe model. In addition, omadacycline groups had more microbial and bile acid diversity compared to vancomycin groups at day 8, which may signify faster return of colonization resistance, a critical attribute when treating CDI. This corresponds to previous literature showing omadacycline does not induce CDI in vitro and that tetracyclines may be protective.

In summary, antibiotic plus germinant combinations were effective at decolonizing mice in this murine model of CDI without causing a detectable burst of toxin production. Although both antibiotic only treatments had similar outcomes in the non-severe model, the addition of germinant solution to either resulted in complete survival. Lastly, in the severe model of CDI, OMC was more effective than VAN. These results indicate omadacycline should be further explored for treatment of CDI. The novel antibiotic-germinant treatment approach has potential to prevent rCDI and decrease spore shedding in healthcare environments.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A germinant mixture comprising
   a) a bile acid main germinant comprising taurocholate, glycocholate, salt thereof, or a combination thereof,
   b) an amino acid co-germinant comprising taurine,
   c) an edible spore solubilizing agent comprising a docusate, and
   d) a calcium salt co-germinant.

2. The germinant mixture of claim 1, comprising
   1 to 5 grams of component a);
   1 to 6 grams of component b);
   200 to 600 milligrams of component c); and
   1 to 8 grams of component d).

3. The germinant mixture of claim 1, wherein b) the amino acid co-germinant further comprise
   glycine.

4. The germinant mixture of claim 1, wherein the calcium salt is calcium carbonate, calcium gluconate, calcium chloride, or calcium citrate.

5. The germinant mixture of claim 1, wherein the a) bile acid main germinant is
   sodium taurocholate, the c) edible spore solubilizing agent is
   sodium docusate or calcium docusate, and the
   d) calcium salt is calcium carbonate or calcium gluconate.

6. The germinant mixture of claim 1, further comprising an antibiotic.

7. The germinant mixture of claim 6, further comprising an antibiotic that is active against *C. difficile*.

8. The germinant mixture of claim 7, wherein the antibiotic comprises vancomycin, omadacycline, fidaxomicin, ridinilazole, or metronidazole.

9. An oral pharmaceutical composition comprising the germinant mixture of claim 8 and a pharmaceutically acceptable excipient.

10. A method of treating, decolonizing, and/or preventing *C. difficile* infection in the gastrointestinal tract of a patient in need thereof, comprising orally administering the oral pharmaceutical composition of claim 9.

11. The method of claim 10, wherein the oral pharmaceutical composition is administered one to two times daily after *C. difficile* symptoms subside, for three to five days, followed one to two days of antibiotic only.

12. The method of claim 10, wherein the oral pharmaceutical composition is administered one to two times daily after a symptom of *C. difficile* infection in the patient subsides.

13. The method of claim 12, wherein the symptom is diarrhea, abdominal pain, fever, or a combination thereof.

14. The method of claim 10, wherein the subject is suffering from recurrent *C. difficile* infection.

15. The method of claim 14, wherein the subject is suffering from recurrent *C. difficile* infection.

16. The method of claim 14, wherein the oral pharmaceutical composition is administered one to two times daily after a symptom of *C. difficile* infection in the patient subsides.

17. The method of claim 16, wherein the symptom is diarrhea, abdominal pain, fever, or a combination thereof.

18. The method of claim 10, wherein the patient is in a hospital or long-term care facility and the *C. difficile* infection follows administration of an antibiotic.

19. The method of claim 10, wherein the patient has a positive stool sample test for *C. difficile*.

20. A germinant mixture comprising
   a) a bile acid main germinant comprising taurocholate, glycocholate, a salt thereof, or a combination thereof,
   b) an amino acid co-germinant comprising taurine,
   c) an edible spore solubilizing agent comprising docusate,
   d) a calcium salt co-germinant, and
   e) omadacycline.

* * * * *